United States Patent
Pratt et al.

(10) Patent No.: US 10,478,643 B2
(45) Date of Patent: *Nov. 19, 2019

(54) HAIR DYEING COMPOSITION

(71) Applicant: KAO GERMANY GMBH, Darmstadt (DE)

(72) Inventors: Dominic Pratt, Darmstadt (DE); Bernd Nöcker, Darmstadt (DE); Fariba Ghiasi, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 81 days.

This patent is subject to a terminal disclaimer.

(21) Appl. No.: 15/566,117

(22) PCT Filed: Apr. 14, 2016

(86) PCT No.: PCT/EP2016/058201
§ 371 (c)(1),
(2) Date: Oct. 12, 2017

(87) PCT Pub. No.: WO2016/166201
PCT Pub. Date: Oct. 20, 2016

(65) Prior Publication Data
US 2018/0111011 A1 Apr. 26, 2018

(30) Foreign Application Priority Data
Apr. 16, 2015 (EP) .................... 15163812

(51) Int. Cl.
*A61Q 5/10* (2006.01)
*A61Q 5/06* (2006.01)
*A61K 8/44* (2006.01)
*A61K 8/49* (2006.01)
*A61K 8/46* (2006.01)

(52) U.S. Cl.
CPC ............... *A61Q 5/065* (2013.01); *A61K 8/44* (2013.01); *A61K 8/447* (2013.01); *A61K 8/466* (2013.01); *A61K 8/49* (2013.01); *A61K 8/494* (2013.01)

(58) Field of Classification Search
CPC ........ A61Q 5/065; A61K 8/4926; A61K 8/44; A61K 8/496; A61K 2800/432; A61K 8/49; A61K 8/447; A61K 8/466
See application file for complete search history.

(56) References Cited

U.S. PATENT DOCUMENTS

| | | | |
|---|---|---|---|
| 5,104,413 A | 4/1992 | Ikeda | |
| 2002/0010970 A1* | 1/2002 | Cottard | A61K 8/342 8/405 |
| 2004/0019982 A1* | 2/2004 | Pratt | A61K 8/466 8/405 |

FOREIGN PATENT DOCUMENTS

| | | | |
|---|---|---|---|
| EP | 2 191 864 A1 | 6/2010 | |
| EP | 2 606 875 A1 | 6/2013 | |
| EP | 2606875 A1 * | 6/2013 | ............... A61Q 5/06 |
| WO | 2010/032034 A2 | 3/2010 | |

OTHER PUBLICATIONS

STIC Search Report dated Feb. 7, 2019.*
International Search Report dated May 11, 2016, dated May 19, 2016.

* cited by examiner

*Primary Examiner* — Eisa B Elhilo
(74) *Attorney, Agent, or Firm* — Norris McLaughlin, P.A.

(57) ABSTRACT

The present invention relates to a hair dyeing composition comprising select hair direct dyes and a reducing agent in order to color hair homogeneously, intensively and durably.

13 Claims, No Drawings

HAIR DYEING COMPOSITION

This application is the U.S. National Stage of International Application No. PCT/EP2016/058201, filed Apr. 14, 2016, which claims foreign priority benefit under 35 U.S.C. § 119 of European Application No. 15163812.9 filed Apr. 16, 2015.

The present invention relates to a hair dyeing composition comprising select hair direct dyes and a reducing agent in order to color hair homogeneously, intensively and durably.

Hair dyeing compositions based on direct dyes have been known for many decades. They are known to color hair somewhat intensively but very often provide difficulty in coloring hair homogenously and durability which has always been an issue as the dyes mostly, if not always, are readily water soluble and/or solubilized by the subsequently used products and therefore are washed out easily from hair which leads to very short lifetime. Therefore, consumers must color their hair more often.

Recently, there have been attempts to achieve intensive colors with compositions comprising the known direct dyes and a reducing agent. In WO 2010/32034 a two-step method is disclosed for coloring hair wherein a sulfur containing nucleophile is applied in the first step and in a second step a dye solution excluding the reactive dyes is brought in contact with hair.

Similarly, a two-step coloring and restructuring process is disclosed in US 2006096042 using oxidative dyes and a hair reducing agent. The method requires an additional intermediate step between the application of oxidative dyeing agent and reducing agent comprising composition.

In U.S. Pat. No. 5,104,413 Kao Corporation has disclosed a composition comprising cysteine derivative known as reducing agents, glutation, an aromatic alcohol which may be ethoxylated and a direct dye.

WO 2013150269 claims a composition comprising a water soluble dye with sulfonate and/or carboxylate groups, urea, thiol and a sulfite salt in the presence of low level of ammonia.

The state of the art so far known as summarized above does not help to solve the problems of homogeneous and intensive coloration of hair with a composition comprising direct dyes. Especially in case of damaged hair it is usually, if not always, observed that the less damaged hair parts and damaged hair parts are colored very much inhomogenously due to different dye uptake properties. This leads to consumer dissatisfaction which requires urgent attention.

The inventors of the present invention have unexpectedly and surprisingly found out that an aqueous composition comprising selected direct dyes and a reducing agent colors the hair much more intensively than the compositions disclosed in the prior art and, more importantly, the colors achieved are exceptionally homogeneous and long lasting.

Thus the first object of the present invention is a ready to use aqueous composition for coloring hair comprising one or more direct dyes selected from the compounds

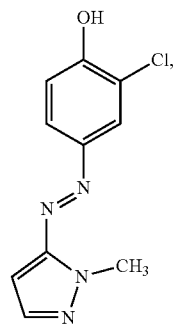

I

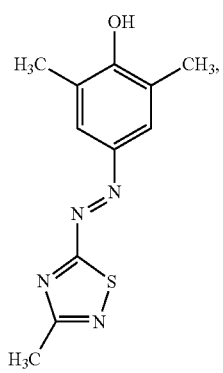

II

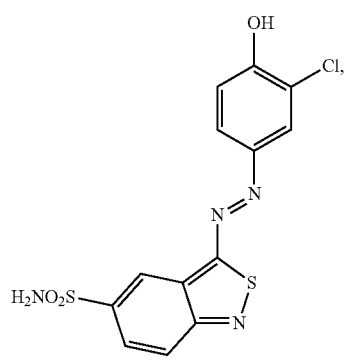

III

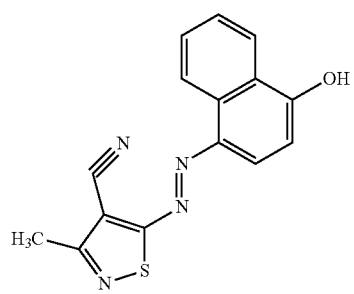

IV and

-continued

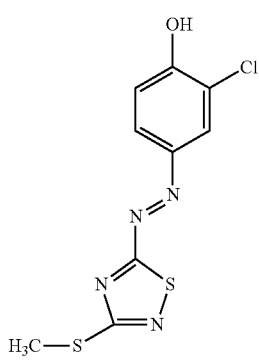

V and one or more reducing agent.

It has furthermore been observed that part of the dyes may undergo a reaction with the reducing agents if they are stored for a relatively long period of time in the same environment and, therefore, the aqueous composition comprising the both must be prepared prior to application onto hair in order to secure optimal results. Therefore, the second object of the present invention is a two-part aqueous hair dying composition comprising the parts A and B which are mixed prior to application onto hair wherein the part A is an aqueous composition comprising one or more dyes selected form the above given dyes and the part B is an aqueous composition comprising one or more reducing agent.

In a further embedment of the present invention the two aqueous compositions of above may also be brought in contact with the hair in a two-step application wherein the part B, comprising one or more reducing agents, is applied onto hair and after leaving on the hair and without rinsing off from the hair, the part A, comprising one or more direct dyes of above is applied and after leaving on the hair for 1 to 45 min rinsed off from hair and hair is optionally shampooed and dried.

Further object of the present invention is the use of the composition for dyeing hair especially for intensive and homogenous dyeing hair.

Another object is the process for coloring hair wherein a composition of the present invention is applied onto hair and after leaving for a period of 1 to 45 min rinsed off from hair and hair is optionally shampooed and dried.

The one or more direct dyes of above are comprised in the aqueous compositions at a total concentration of 0.001 to 10%, preferably 0.01 to 7.5%, more preferably 0.05 to 5% and most preferably 0.1 to 4% by weight calculated to the total of the compositions. It should be noted that the compositions may comprise other direct dyes. The concentrations referred to here are the total direct dye concentration in the compositions.

The aqueous compositions comprise one or more reducing agents. The suitable non-limiting reducing agents are thioglycolic acid and its salts such as sodium, potassium and ammonium, thiolactic acid and it salts such as sodium, potassium and ammonium, dihydrolipoate, thioglycerol, mercapropionic acid and its salts such as sodium, potassium and ammonium, cysteine and its salts, N substituted cysteins, cystamines, thioethanol, sulfite salts such as sodium, potassium and ammonium, bisulfite salts such as sodium, potassium and ammonium and metabisulfite salts such as sodium, potassium and ammonium. The preferred ones are thioglycolic acid and its salts, thiolactic acid and it salts, cysteine and its salts, N substituted cysteins, cystamines, sulfite salts such as sodium, potassium and ammonium, bisulfite salts such as sodium, potassium and ammonium and metabisulfite salts such as sodium, potassium and ammonium. The particularly suitable ones are thioglycolic acid and its salts such as sodium, potassium and ammonium, and sulfite salts such as sodium, potassium and ammonium.

The reducing agents are comprised in the compositions at a total concentration of 0.001 to 10%, preferably 0.01 to 7.5%, more preferably 0.05 to 5% and most preferably 0.1 to 4% by weight calculated to the total of the compositions.

The composition of the present invention can comprise additionally direct dyes of neutral, cationic and anionic character. Some examples to suitable cationic dyes are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14 and Basic Yellow 57. According to the invention, suitable cationic dyestuffs are in principal those any available on the market for cosmetic hair colouring applications. For this purpose, special reference is made to the PCT application WO 95/15144 of Ciba-Geigy AG. The content of the PCT application WO 95/15144 is by reference incorporated here.

Examples to suitable direct acting anionic dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Some examples to those suitable neutral dyes (HC dyes), including nitro dyes, are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzene, 1,4-Diamino-2-nitrobenzene, 3-Nitro-4-aminophenol, 1-Hydroxy-2-amino-3-nitrobenzene and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

The compositions comprise additionally one or more alkalizing agents. The suitable alkalizing agents are ammonia and a compound according to the general structure

wherein $R_9$, $R_{10}$ and $R_{11}$ are same or different H, $C_1$-$C_6$ alkyl, $C_1$-$C_6$ monohydroxyalkyl or $C_2$-$C_6$ polyhydroxyalkyl with the condition that at least one of $R_9$, $R_{10}$ and $R_{11}$ is a mono or polyhydroxyalkyl, preferably $R_9$, $R_{10}$ and $R_{11}$ are same or different H, $C_1$-$C_4$ alkyl, $C_1$-$C_4$ monohydroxyalkyl or $C_2$-$C_4$ polyhydroxyalkyl with the condition that at least one of $R_9$, $R_{10}$ and $R_{11}$ is a mono or polyhydroxyalkyl, more preferably $R_9$, $R_{10}$ and $R_{11}$ are same or different H, $C_2$-$C_4$ alkyl, $C_2$-$C_4$ monohydroxyalkyl or $C_2$-$C_4$ polyhydroxyalkyl with the condition that at least one of $R_9$, $R_{10}$ and $R_{11}$ is a mono or polyhydroxyalkyl, Suitable alkanolamines according to the general formula of above are monoethanolamine, diethanolamine, triethanolamine, aminomethyl propanol, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine, triethanolamine and aminomethyl propanol. The most preferred are monoethanolamine and aminomethyl propanol The concentration of alkalizing agent in the composition varies between 0.5 and 35%, preferably 1 and 30, more preferably 2.5 and 25 and most preferably 2.5 to 20% by weight calculated to the total composition.

The composition preferably comprises one or more organic solvents. Suitable are ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. The total concentration of one or more organic solvents is in the range of 0.1 to 25%, preferably 0.2 to 20%, more preferably 0.5 to 15% and most preferably 1 to 10% by weight, calculated to the total of the composition.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05 to 1% by weight, calculated to the total composition.

The aqueous composition may be in the form of a solution, emulsion, cream, gel and mousse.

Compositions of the present invention may be in the form of emulsions and comprise therefore fatty alcohol, oil and surfactants as emulsifiers.

The fatty alcohols preferred are according to the following general structure

wherein $R_1$ is a linear or branched, saturated or unsaturated alkyl chain with 12 to 22 C atoms. Suitable fatty alcohols are myristyl alcohol, cetyl alcohol, stearyl alcohol and behenyl alcohol and their mixtures. Most preferred is the mixture of cetyl and stearyl alcohol also known as cetearyl alcohol.

The concentration of one or more fatty alcohols is in the range of 1 to 25%, preferably 1 to 20%, more preferably 1.5 to 15% and most preferably 1.5 to 10% by weight calculated to total composition.

Compositions comprise oil, which may be natural and/or synthetic. Concentration of oil varies between 0.1 and 25%, preferably 0.5 and 25% and more preferably 1 and 20%, most preferably 2 and 20%, in particular 2.5 and 15% by weight calculated to the total composition.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil. Preferred are argan oil, shea butter oil, karite oil, olive oil, almond oil, avocado oil, ricinus oil, coconut oil, palm oil, sesame oil, peanut oil, whale oil, sunflower oil, peach kernel oil, wheat germ oil, macadamia nut oil, macadamia oil, night primrose oil, jojoba oil, castor oil, and soya oil. More preferred are argan oil, shea butter oil, karite oil, macadamia nut oil, macadamia oil, olive oil, almond oil, avocado oil, ricinus oil, coconut oil, palm oil, sesame oil, peanut oil, sunflower oil, peach kernel oil, wheatgerm oil, jojoba oil, castor oil, and soya oil. Most preferred are argan oil, shea butter oil, karite oil, olive oil, almond oil, avocado oil, coconut oil, macadamia nut oil, macadamia oil, palm oil, sesame oil, peach kernel oil, wheatgerm oil, jojoba oil, and soya oil. Particularly preferred are argan oil, shea butter oil and karite oil which may be comprised as a single oil component or in admixture with each other.

Further suitable oil components are natural oils such as mineral oil.

Further suitable ones are synthetic oils such as silicones known with CTFA adopted name dimethicone, cyclomethicone, and arylated silicones such as phenyl trimethicone which are available commercially from Dow Corning.

Further suitable synthetic oils are fatty acid fatty alcohol esters such as octyl palmitate, isocetyl palmitate, isopropyl palmitate and octyl stearate.

Compositions preferably comprise one or more surfactants as emulsifiers. Suitable surfactants are non-ionic, cationic, anionic ones and their mixtures.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants. Preferred are alkyl sulphates or alkyl ether sulphates and the most preferred are alkyl ether sulphates.

Further surfactants in the compositions according to the invention are nonionic surfactants. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates. Further nonionic surfactants preferred in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 50, preferably about 10 and about 20. The most preferred is ceteth, steareth and ceteareth with 20 to 35 ethoxy groups and ceteareth-30 is particularly preferred.

Compositions may comprise a cationic surfactant and especially a monoalkyl cationic surfactant according to the general structure

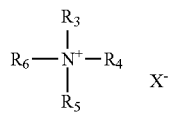

where $R_3$ is a saturated or unsaturated, branched or linear alkyl chain with 8-22 C atoms or

where $R_7$ is saturated or unsaturated, branched or linear alkyl chain with 7-21 C atoms and n has typical value of 1-4 or

where $R_8$ is saturated or unsaturated, branched or linear alkyl chain with 7-21 C atoms and n has typical value of 1-4, and $R_4$, $R_5$ and $R_6$ are H or lower alkyl chain with 1 to 4 Carbon atoms, and X is typically chloride, bromide, methosulfate.

Typical examples of those ingredients are cetyl trimethyl ammonium chloride, stear trimonium chloride, palmitoyl trimonium chloride, stearamidopropyl trimonuim chloride and oleoylethyl trimethyl ammonium methosulfate. The most preferred are cetyl trimethly ammonium chloride, stear trimonium chloride and palmitoyl trimonium chloride. Cetyl trimethyl ammonium chloride is particularly preferred.

The total concentration of one or more surfactants is in the range of 0.1 to 25%, preferably 0.2 to 20%, more preferably 0.5 to 15% and most preferably 1 to 10% by weight calculated to total composition.

Further, compositions may comprise polymers selected from the group consisting of cellulose polymer, alginate, polysaccharides and acrylic acid polymers, preferably methyl cellulose, ethyl cellulose, hydroxyethylcellulose, methylhydroxyethylcellulose, methylhydroxypropylcellulose, carboxymethyl cellulose, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total concentration of 0.1 to 15%, preferably from 0.2 to 10%, and more preferably in an amount of from 0.5 to 7.5% by weight, calculated to total composition.

Composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Typical concentration range for any of the cationic polymers is in the range of 0.1 to 2.5%, preferably 0.2-2% and more preferably 0.25-1.5% by weight, calculated to the total of the composition.

The pH of the composition is in the range of 2 to 11, preferably 6 to 10.5, more preferably 7 to 10 and most preferably 8 to 9.5. The pH is measured at ambient temperature, preferably at 20° C.

Compositions may comprise additionally one or more chelating agent. In principal any chelating agent known in the field of cosmetics is suitable for the compositions of the present invention. Preferred are ethylene diamine tetraacetic acid (EDTA) etidronic acid, galactaric acid, gluconic acid and therei respective salts. Most preferred are ethylene diamine tetraacetic acid (EDTA) etidronic acid and gluconic acid and their respective salts and also their mixtures.

In cases where the reducing agent is comprised in the composition at a relatively higher concentration, i.e. above 2.5% by weight calculated to the total of the composition, reduction of disulphide bonds may be caused which may require an additional fixing step in order to re-establish disulphide bonds after dyeing hair with an acidic oxidizing composition comprising 0.1 to 12% by weight oxidizing agent preferably hydrogen peroxide.

The composition of the present invention may be provided in a form of kit for hair which comprises one or more compositions wherein one of the compositions is a ready to use composition of the present invention. In case where reducing and coloring agents are comprised in two different compositions, the kit of the present invention comprises two or more compositions wherein one is an aqueous composition comprising one or more direct dyes of the above given structures and the other aqueous composition comprises one or more reducing agents.

The following examples are to illustrate the invention but not to limit it.

EXAMPLE 1

Dye Composition

|  | % by weight |
| --- | --- |
| Dyestuff | 0.2 |
| Isopropanol | 5.0 |
| Phenoxyethanol | 2.0 |
| Monoethanolamine | 3.2 |
| Ammonium chloride | 1.0 |
| Water | q.s. to 100 |

The pH of the above composition is 10.0

Reducing Composition

|  | % by weight |
| --- | --- |
| Isopropanol | 5.0 |
| Thioglycolic acid | 2.0 |
| Monoethanolamine | 6.0 |
| Ammonium chloride | 1.0 |
| Water | q.s. to 100 |

The pH of the above composition is 10.0

Composition without Reducing Agent

|  | % by weight |
| --- | --- |
| Isopropanol | 5.0 |
| Monoethanolamine | 6.0 |
| Ammonium chloride | 1.0 |
| Water | q.s. to 100 |

The pH of the above composition is 10.0

The dyestuffs used were the compound III according to the invention and Acid Black 1 according to the prior art (comparative composition)

The hair (natural human hair at a colour level 7) colouring was carried out by application of the dyeing composition after mixing the dyeing composition with reducing composition (for comparative purposes with the composition without reducing agent) at a weight ratio of 1 to 1 onto hair and leaving on the hair for 30 min at room temperature and rinsing it off from hair. After drying the hair colour was measured with a laboratory colorimeter and color differences ($\Delta E$) were calculated between uncoloured and coloured tresses. The results are as follows:

|  | $\Delta E$ |
| --- | --- |
| HC Blue 18 | 24.1 |
| HC Blue 18 + 1% TGA | 30.9 |
| Acid Black 1 + 1% TGA | 19.2 |

The above results clearly demonstrates that addition of reducing agent to the dyeing composition increase colour intensity (the $\Delta E$ is higher) and the blue dye according to the invention colours hair more intensively than the dye known from the prior art.

In order to demonstrate homogeneous colouration of hair, the above dyeing compositions were applied onto natural and permanently shaped goat hair in the same way as described above. The results are as follows:

|  | Delta E values | |
| --- | --- | --- |
|  | Goat | Goat Permed |
| HC Blue 18 | 64.1 | 76.3 |
| HC Blue 18 + 1% TGA | 71.4 | 77.4 |
| Acid Black 1 + 1% TGA | 49.0 | 64.5 |

The above results clearly show that the dyeing composition according to present invention colours natural and permanently shaped hair homogeneously whereas the composition without reducing agent may not achieve the same homogeneity. The dyeing composition according to the literature does not provide homogeneous colour on goat hair.

EXAMPLE 2

Ready to Use Dyeing Composition

|  | % by weight |
| --- | --- |
| Dyestuff I | 0.2 |
| Isopropanol | 5.0 |
| Phenoxyethanol | 2.0 |
| Thioglycolic acid | 1.2 |
| Monoethanolamine | 3.9 |
| Ammonium chloride | 1.0 |
| Xanthan gum | 1.0 |
| Water | q.s. to 100 |

The pH of the above composition is 10.4

EXAMPLE 3

Ready to Use Dyeing Composition

|  | % by weight |
| --- | --- |
| Dyestuff III | 0.2 |
| Isopropanol | 5.0 |
| Phenoxyethanol | 2.0 |
| Thioglycolic acid | 1.2 |
| Monoethanolamine | 3.2 |
| Ammonium chloride | 1.0 |
| Cetearyl alcohol | 9.0 |
| Sodium laureth sulphate | 3.0 |
| Water | q.s. to 100 |

The pH of the above composition is 9.7

EXAMPLE 4

Ready to Use Dyeing Composition

|  | % by weight |
|---|---|
| Dyestuff V | 0.2 |
| Isopropanol | 5.0 |
| Phenoxyethanol | 2.0 |
| Thioglycolic acid | 1.2 |
| Monoethanolamine | 2.6 |
| Ammonium chloride | 1.0 |
| Cetearyl alcohol | 9.0 |
| Ceteareth-20 | 3.0 |
| Water | q.s. to 100 |

The pH of the above composition is 9.5

EXAMPLE 5

Ready to Use Dyeing Composition

|  | % by weight |
|---|---|
| Dyestuff V | 0.2 |
| Isopropanol | 5.0 |
| Phenoxyethanol | 2.0 |
| Cystein HCl | 1.2 |
| Monoethanolamine | 2.9 |
| Cetearyl alcohol | 9.0 |
| Ceteareth-20 | 3.0 |
| Water | q.s. to 100 |

The pH of the above composition is 9.5

EXAMPLE 6

Ready to Use Dyeing Composition

|  | % by weight |
|---|---|
| Dyestuff V | 0.2 |
| Isopropanol | 5.0 |
| Phenoxyethanol | 2.0 |
| Cystein HCl | 1.2 |
| Ammonium hydroxide | 2.9 |
| Ammonium chloride | 1.0 |
| Cetearyl alcohol | 9.0 |
| Ceteareth-20 | 3.0 |
| Water | q.s. to 100 |

The pH of the above composition is 9.5

| | Example (All values are % by weight) | | | | | |
|---|---|---|---|---|---|---|
| | 7 | 8 | 9 | 10 | 11 | 12 |
| 2-Propanol | 5.00 | 5.00 | 5.00 | 5.00 | 5.00 | 5.00 |
| Benzyl Alcohol | | 1.00 | 2.00 | | | |
| Phenoxyethanol | | | | 2.00 | 2.00 | |
| Ammonium hydroxide (25%) | 5.00 | 5.00 | 5.00 | 5.00 | 5.00 | 5.00 |
| Sodium sulfit | 0.50 | | | | | |
| Ammonium thioglycolate | 2.00 | 2.00 | 2.00 | 2.00 | 2.00 | 2.00 |
| HC Blue 17 | 0.10 | | | | | |
| Basic Yellow 87 | | | | 0.20 | | |
| Basic Red 51 | | 0.20 | | | | |
| 3-Nitro-N-(2-hydroxypropyl)-4-aminophenol | | | 0.20 | | | |
| HC Blue 2 | | | | | | |
| HC Yellow 10 | | | | | | 0.20 |
| Acid Red 52 | | | | 0.30 | | |
| Acid Yellow 3 | | | | | | |
| Acid Violet 43 | | | | | | |
| Dye I (yellow) | 0.2 | | 0.1 | | | |
| Dye III (blue) | | 0.2 | | 0.2 | 0.2 | |
| Dye V (red) | | | | 0.1 | | 0.1 |
| Water | to 100 | to 100 | to 100 | to 100 | to 100 | to 100 |
| pH (adjusted with HCl) | 10 | 10 | 10 | 10 | 10 | 10 |
| Coloring on white goat hair | green | violet | red | brown | purple | orange |

| | Example (All values are % by weight) | | | | |
|---|---|---|---|---|---|
| | 13 | 14 | 15 | 16 | 17 |
| 2-Propanol | 5.00 | 5.00 | 5.00 | 5.00 | 5.00 |
| Benzyl Alcohol | | | | | |
| Phenoxyethanol | | | | | |
| Ammonium hydroxide (25%) | 5.00 | 5.00 | 5.00 | 5.00 | 5.00 |
| Sodium sulfit | | | | | 2.00 |
| Ammonium thioglycolate | 2.00 | 2.00 | 2.00 | 2.00 | 2.00 |
| HC Blue 17 | | | | | |
| Basic Yellow 87 | | | | | |
| Basic Red 51 | | | | | |
| 3-Nitro-N-(2-hydroxypropyl)-4-aminophenol | | 0.20 | | | 0.3 |
| HC Blue 2 | | | 0.2 | | |
| HC Yellow 10 | | 0.10 | | | |
| Acid Red 52 | | | | | |
| Acid Yellow 3 | | | | 0.3 | |
| Acid Violet 43 | 0.40 | | | | |
| Dye I (yellow) | | | | | |
| Dye III (blue) | | 0.3 | | | 0.3 |
| Dye V (red) | 0.1 | | 0.3 | 0.2 | 0.3 |
| Water | to 100 | to 100 | to 100 | to 100 | to 100 |
| pH (adjusted with HCl) | 10 | 10 | 10 | 10 | 10 |
| Coloring on white goat hair | purple | brown | violet | orange-red | violet |

| Formulation, all values in [%] | Example | |
|---|---|---|
| | 18 | 19 |
| Sodium bicarbonate | 15 | 15 |
| EDTA | 2 | 2 |
| Paraffin Oil | 9 | 9 |
| Sodium sulfit | — | 2 |
| Cystein HCl | 2 | — |
| Sodium metasilicate | 8 | 8 |
| Dye III | 1 | 1 |
| Dye V | 1 | 1 |
| Diatomaceous Earth | @100 | @100 |
| Coloring on white goat hair | violet | violet |

Examples 18 and 19 are in powder form.

Dyeing Method

The reductive alkaline dyeing powder base is mixed with water or a water based solution at a weight ratio of e.g. 1:1 and applied onto hair, and after processing 1 to 45 min at ambient temperature, and hair is optionally rinsed off with water and is treated with an oxidizing composition, rinsed off, optionally shampooed and dried.

The invention claimed is:

1. A ready to use aqueous composition for coloring hair comprising one or more direct dyes selected from the compounds

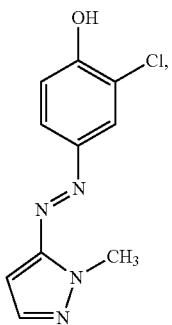
I

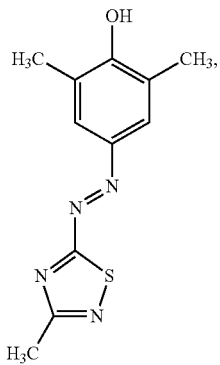
II

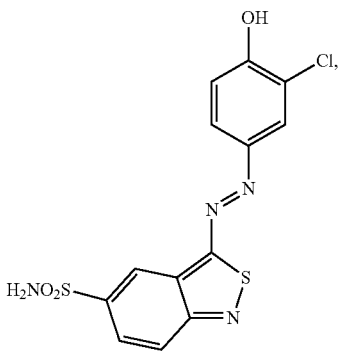
III

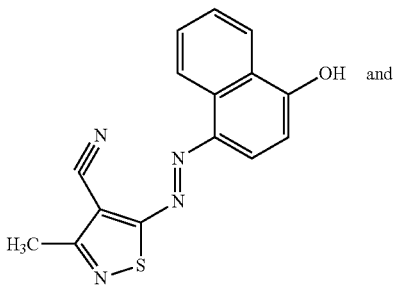 and
IV

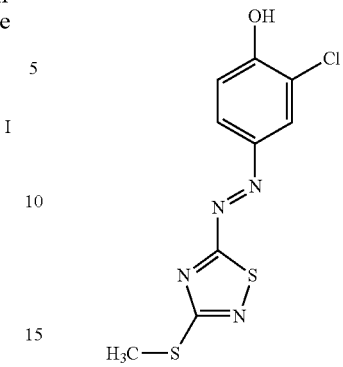
V and one or more reducing agents selected from the group consisting of thioglycolic acid and its salts, thiolactic acid and its salts, dihydrolipoate, thioglycerol, mercapropionic acid and its salts, cysteine and its salts, N substituted cysteins, cystamines, thioethanol, sulfite salts, bisulfite salts, and metabisulfite salts.

2. A two-part aqueous hair coloring composition comprising parts A and B for mixing prior to application onto hair, wherein the part A is an aqueous composition comprising one or more direct dyes selected from the compounds

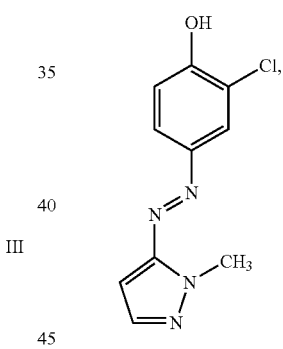
I

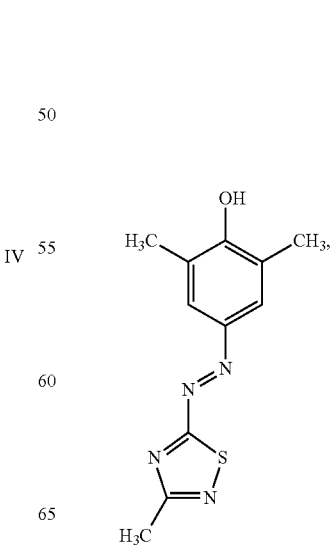
II

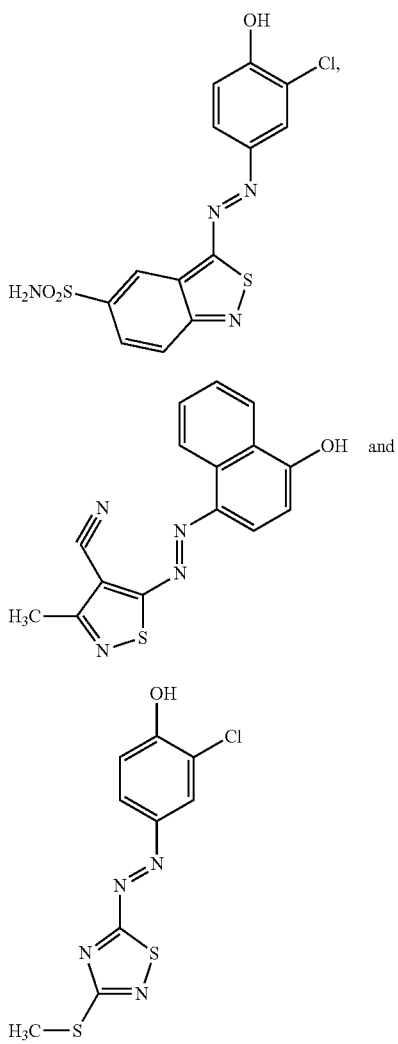

and the part B is an aqueous composition comprising one or more reducing agents selected from the group consisting of thioglycolic acid and its salts, thiolactic acid and its salts, dihydrolipoate, thioglycerol, mercaptopropionic acid and its salts, cysteine and its salts, N substituted cysteins, cystamines, thioethanol, sulfite salts, bisulfite salts, and metabisulfite salts.

3. The composition according to claim 1, wherein the one or more direct dyes are comprised at a concentration 0.001 to 10% by weight, calculated to the total of the composition.

4. The composition according to claim 1, further comprising:
additional direct dyes selected from neutral, cationic and anionic dyes.

5. The composition according to claim 1, wherein the one or more reducing agents are present at a total concentration of 0.001 to 10% by weight, calculated to the total of the composition.

6. The composition according to claim 1, further comprising:
one or more alkalizing agents, at a total concentration in the range between 1 and 35% by weight, calculated to the total of the composition.

7. The composition according to claim 6, wherein the one or more alkalizing agents are selected from ammonia and a compound according to the general structure $$R_9R_{10}R_{11}N$$

wherein $R_9$, $R_{10}$ and $R_{11}$ are same or different H, $C_1$-$C_6$ alkyl, $C_1$-$C_6$ monohydroxyalkyl or $C_2$-$C_6$ polyhydroxyalkyl with the condition that at least one of $R_9$, $R_{10}$ and $R_{11}$ is a mono or polyhydroxyalkyl, $C_1$-$C_4$ monohydroxyalkyl or $C_2$-$C_4$ polyhydroxyalkyl with the condition that at least one of $R_9$, $R_{10}$ and $R_{11}$ is a mono or polyhydroxyalkyl.

8. The composition according to claim 1, further comprising:
one or more organic solvents, at a total concentration in the range of 0.5 to 40% by weight, calculated to the total of the composition.

9. The composition according to claim 1, further comprising:
one or more fatty alcohols.

10. The composition according to claim 1, further comprising:
one or more surfactants selected from non-ionic, anionic and cationic ones.

11. The composition according to claim 1, wherein the composition has a pH in the range of 2 to 11.

12. A process for coloring hair, the process comprising:
applying the composition according to claim 1 onto hair for a period of 1 to 45 min;
rinsing the composition off from the hair; and
drying the hair.

13. The process according to claim 12, further comprising:
shampooing the hair with an additional composition comprising oxidizing agent before drying the hair.

* * * * *